US006441246B1

(12) United States Patent
Yamamoto et al.

(10) Patent No.: US 6,441,246 B1
(45) Date of Patent: Aug. 27, 2002

(54) CATALYTIC SYNTHESIS OF ALDEHYDES BY DIRECT HYDROGENATION OF CARBOXYLIC ACIDS

(75) Inventors: Akio Yamamoto, Tokyo; Kazuhiro Nagayama, Higashimurayama, both of (JP)

(73) Assignee: Japan Science And Technology Corporation, Saitama-ken (JP)

( * ) Notice: Subject to any disclaimer, the term of this patent is extended or adjusted under 35 U.S.C. 154(b) by 0 days.

(21) Appl. No.: 09/763,922

(22) PCT Filed: Aug. 27, 1999

(86) PCT No.: PCT/JP99/04633

§ 371 (c)(1),
(2), (4) Date: Jul. 24, 2001

(87) PCT Pub. No.: WO00/12457

PCT Pub. Date: Mar. 9, 2000

(30) Foreign Application Priority Data

Aug. 27, 1998 (JP) ............................................. 10-241651

(51) Int. Cl.[7] ................................................ C07C 45/41
(52) U.S. Cl. ........................ 568/485; 568/484; 568/449; 568/426
(58) Field of Search ................................. 568/426, 449, 568/485, 484

(56) References Cited

FOREIGN PATENT DOCUMENTS

| JP | 4-210936 A | 3/1992 |
| JP | 9-40599 A | 10/1997 |

OTHER PUBLICATIONS

K. Nagayama et al., "Direct Hydrogenation of Carboxylic Acids to Aldehydes Catalyzed by Palladium Complexes in the Presence of Pivalic Anhydride", Chem. Lett., 1998, No. 11, p. 1143–1144.

*Primary Examiner*—Sreeni Padmanabhan
(74) *Attorney, Agent, or Firm*—Peter F. Corless; Edward J. Adamson; Edwards & Angell, LLP

(57) ABSTRACT

A process which makes it possible to prepare aldehydes under mild reaction conditions with a high efficiency through the reduction of carboxylic acids with molecular hydrogen. Specifically, a process of reducing an organic carboxylic acid with molecular hydrogen in the presence of a catalyst into an aldehyde corresponding to the acid, characterized by conducting the reduction in the presence of a dehydrating agent such as a carboxylic anhydride.

18 Claims, No Drawings

CATALYTIC SYNTHESIS OF ALDEHYDES BY DIRECT HYDROGENATION OF CARBOXYLIC ACIDS

This is a US National Stage Application of PCT/JP99/04633 filed Aug. 27, 1999 now WO 00/12457 published Nov. 9, 2000.

FIELD OF THE INVENTION

This invention provides a method for simple and highly efficient preparation of aldehydes in which organic carboxylic acids are reduced to corresponding organic aldehydes with molecular hydrogen in the presence of catalysts, wherein said reaction is performed in the presence of a dehydrating agent.

BACKGROUND ART

Aldehydes are used, not only for perfume, drugs and agricultural chemicals by themselves but also as raw materials for synthesis of fine chemicals. As the conventional procedures of aldehyde synthesis, the methods such as oxidation of hydrocarbons and reduction of acid halides are known, but these methods have problems such as poor reaction efficiency including critical oxidation conditions and stoichiometric formations of by-products such as halides, in addition to heavy environmental load.

As the methods to prepare aldehydes by reducing carboxylic acids, typically multi-step reactions are used, for example, converting carboxylic acids to acid chlorides and the like followed by partial reduction thereof, or converting the acids to alcohols followed by partial oxidation thereof.

An aldehyde synthesis reaction by catalytic hydrogenation of acid chlorides using molecular hydrogen as a hydrogen source in the presence of solid palladium catalysts is called the Rosenmund reduction, and is known to proceed almost quantitatively in various substrates by adding amines to the reaction system. This reaction has such advantages that hydrogen pressure can be the atmospheric pressure, but also disadvantages such as necessity of preparing acid chlorides and generation of acidic hydrochloric acid as a by-product. There is a report of hydrogenation in homogeneous system using palladium complexes. However, this reaction is limited to the substrates of aromatic carboxylic acid chlorides (A. Schoenberg and R. F. Heck, J. Am. Chem. Soc., 96, 7761(1974)).

A method developed by former Mitsubishi Chemical Ind. (presently Mitsubishi Chemical Corp.) is an example of efficient hydrogenation of carboxylic acids using molecular hydrogen. This process provides aldehydes selectively in high yield by hydrogenation in vapor phase at high temperature (330–400° C.) in the presence of zirconia or chromic acid based solid catalysts (N. Ding, J. Kondo, K. Maruya, K. Domen, T. Yokoyama, N. Fujita, T. Maki, Catal., 17, 309 (1993); laid-open Japanese Patent 1992-210936 (T. Yokoyama et al.); laid-open Japanese Paten 1987-108832 (T. Maki et al.); general review: T. Yokoyama, Monthly Report of Japan Chem. Ind. Association, April, 1997, p.14). Disadvantages of this method are difficulties in applications to the substrates with poor heat stability because high temperature is required for the reaction, and to a unit reaction in small-scale synthesis due to large sized plant being required.

The inventors of this invention have reported a method for preparation of aldehydes by reducing carboxylic anhydrides using molecular hydrogen under mild reaction conditions in the presence of zero valent palladium complex catalysts (Chem. Lett. 1995, 365). However, this method has problems in reaction efficiency such as necessity of preparation of acid anhydrides as raw materials in advance and generation of carboxylic acids equimolar to aldehydes as by-products.

BRIEF DESCRIPTION OF THE INVENTION

The invention provides a method for highly efficient preparation of aldehydes under mild reaction conditions by reducing carboxylic acids using molecular hydrogen.

The invention relates to a method for preparation of aldehydes in which organic carboxylic acids are reduced to corresponding organic aldehydes using molecular hydrogen in the presence of catalysts, wherein said reaction is performed in the presence of dehydrating agents.

MOST PREFERRED EMBODIMENT OF THIS INVENTION

In order to improve yield in the above mentioned preparation method for aldehydes using carboxylic anhydrides as raw materials (Chem. Lett. 1995, 365), the inventors have studied enthusiastically on an improvement of this reaction system. As the results, it was unexpectedly found that aldehydes was able to be obtained in high yield by converting corresponding carboxylic acids of raw materials to carboxylic anhydrides in this reaction system in the presence of dehydrating agents.

Thus, the invention features to obtain aldehydes in high yield by hydrogenating carboxylic acids with generation of acid anhydrides in the reaction system, in coexistence of dehydrating agents such as trimethylacetic anhydride.

There is no specific limitation on the dehydrating agents in the invention so long as they can convert carboxylic acids of raw materials to corresponding carboxylic anhydrides or mixture thereof in the reaction conditions, and more specifically, the compounds such as carboxylic anhydrides, dicarbonates or carbodiimides may be used, among which carboxylic anhydrides are preferred.

Carboxylic anhydrides to be used as dehydrating agent include linear or branched aliphatic carboxylic anhydrides having from 1 to 20, preferably from 1 to 10 carbon atoms; aromatic carboxylic anhydrides having from 6 to 20, preferably from 6 to 12 carbon atoms; and the like. Preferred carboxylic anhydrides include branched aliphatic carboxylic anhydrides having from 1 to 20, preferably from 1 to 10 carbon atoms. More typically, carboxylic anhydrides with sterically bulky substituents, such as trimethyl acetic anhydride, are more preferable.

Organic carboxylic acid as starting material of the invention may be any compound having carboxylic groups, and also may have other groups within the molecule that do not give any adverse effect on the reaction of the invention. When the carboxylic acids have groups with adverse effects on the reaction of the invention, the acids can be provided to the reaction after protecting the said groups with suitable protection groups generally used in peptide synthesis, etc.

Organic carboxylic acids as starting materials of the invention can be expressed by the following general formula (I), $$R\text{---}COOH \qquad (I)$$

(wherein, R is an organic group)

and the organic group of R includes optionally substituted alkyl, optionally substituted alkenyl, optionally substituted alkynyl, optionally substituted cycloalkyl, optionally substituted cycloalkenyl, optionally substituted aryl, optionally substituted heteroaryl and the like.

These organic carboxylic acids may be monocarboxylic acids or polybasic acids having plural carboxyl groups such as dicarboxylic acids, tricarboxylic acids and the like.

Preferred alkyl groups in the general formula (I) above include linear or branched alkyl groups having from 1 to 30, preferably from 1 to 20, and more preferably from 5 to 15 carbon atoms; preferred alkenyl groups include linear or branched alkeny) groups having from 2 to 30, preferably from 2 to 20, and more preferably from 5 to 15 carbon atoms; preferred cycloalkyl groups include cycloalkyl groups of monocyclic, polycyclic or condensed ring system, having from 5 to 30, preferably from 5 to 20, and more preferably from 6 to 10 carbon atoms; preferred cycloalkenyl groups include aforementioned cycloalkyl groups having at least one unsaturated bond; preferred aryl groups include aryl groups of monocyclic, polycyclic or condensed ring system, having from 6 to 30, preferably from 6 to 20, and more preferably from 6 to 10 carbon atoms; and preferred heteroaryl groups include saturated or unsaturated heteroaryl groups of monocyclic, polycyclic or condensed ring system, containing at least one nitrogen, oxygen or sulfur atom, each ring having from 5 to 20, preferably from 5 to 10, and more preferably from 5 to 7 of ring members, wherein the groups may have cycloalkyl, cycloalkenyl or aryl groups described above in a condensed form. Or, R groups may be so-called aralkyl groups and may include aforementioned alkyl or alkenyl groups substituted by aryl or heteroaryl groups described above.

Alkyl, alkenyl, cycloalkyl, cycloalkenyl, aryl, heteroaryl or aralkyl groups in the general formula (I) above may be substituted by substituents not adversely affecting on the reaction. If the substituents have possibilities to adversely affect the reaction, such substituents can also be protected with protecting groups. Therefore, substituents in this invention also include reactive substituents that may be protected with protection groups during the reaction.

Alkyl, alkenyl, cycloalkyl, cycloalkenyl, aryl, heterocyclic or aralkyl groups in the general formula (I) above may be mutually substituted, if such mutual substitutions are possible. For example, the groups such as alkyl-substituted cycloalkyl groups, alkyl-substituted aryl groups, alkyl-substituted heteroaryl groups, alkyl-substituted aralkyl groups, cycloalkyl-substituted alkyl groups, cycloalkyl-substituted alkenyl groups and alkeny-substituted aryl groups are included.

Other substituents include alkoxy groups, alkylthio groups, dialkylamino groups, alkoxy carbonyl groups consisting of alkyl groups described above; halogen atoms such as chlorine, bromine and fluorine; alkylenedioxy groups such as methylenedioxy, 2,2-dimethylmethylenedioxy groups; cyano groups; and the like.

Preferred substituents include lower alkyl groups such as methyl, ethyl, n-propyl, isopropyl and t-butyl groups; aryl groups such as phenyl and naphthyl groups; lower alkoxy groups such as methoxy, ethoxy and n-propoxy groups; lower alkylamino groups such as dimethylamino, diethylamino and dipropylamino groups; alkoxycarbonyl groups such as methoxycarbonyl and ethoxycarbonyl groups; halogen atoms such as chlorine and fluorine; alkylenedioxy groups such as methylenedioxy and 2,2-dimethylmethylenedioxy groups; cyano groups; and the like.

Typical examples of R in the general formula (I) above include, e.g., lower alkyl groups such as methyl, ethyl, n-propyl, isopropyl, n-butyl, t-butyl and hexyl groups; lower alkenyl groups such as vinyl, propenyl and butenyl groups; cycloalkyl groups such as cyclohexyl and cyclopentyl groups; cycloalkenyl groups such as cyclohexenyl group; aryl groups such as phenyl and naphthyl groups; heterocyclic groups such as thienyl and furanyl groups; aralkyl groups such as benzyl and phenethyl groups; and the like.

Carboxylic acids as starting materials in this invention include, for example, aliphatic carboxylic acids such as caprylic acid, n-caproic acid, 2-methylvaleric acid, lauric acid and palmitic acid; aliphatic dicarboxylic acids such as adipic acid, pimelic acid, sebacic acid and dodecanoic dicarboxylic acid; esters of aliphatic polycarboxylic acids such as monomethyl adipate, monoethyl pimelate, monoethyl sebacate and monoethyl dodecanoic dicarboxylate; aliphatic unsaturated carboxylic acids such as oleic acid, crucic acid and 10-undecenoic acid; aliphatic carboxylic acids with aromatic substituents such as phenylacetic acid, diphenylacetic acid, 2-phenylpropionic acid, 3-phenylpropionic acid and cinnamic acid; cyclic aliphatic acids such as cyclohexanecarboxylic acid; aromatic carboxylic acids such as benzoic acid, 2-naphthoic acid, 4-cyanobenzoic acid, 4-t-butylbenzoic acid, 4-methoxybenzoic acid, 3-phenoxybenzoic acid, 2-methylbenzoic acid and 3,4-methylenedioxybenzoic acid; aromatic dicarboxylic acids such as terephthalic acid; aromatic tricarboxylic acids such as 1,3,5-benzenetricarboxylic acid; heteroaryl carboxylic acids such as pyridinecarboxylic acid, furancarboxylic acid and thiophenecarboxylic acid; and the like.

Amount of the dehydrating agent of the invention may be catalytic level, however, a higher level is more preferable. For example, the amount is not less than 1 equivalent, preferably, from 1 to 10 equivalent, more preferably, from 2 to 5 equivalent, still more preferably, from 3 to 5 equivalent to the carboxylic acid of raw material.

As the catalyst of the invention, conventional hydrogenation catalysts may be suitably used, however, catalysts of transition metal or noble metal are preferable. The catalysts of the invention may be used as a homogeneous catalyst by making them soluble or in a heterogeneous system as solid catalysts.

Transition metal or noble metal catalysts include palladium, cobalt and platinum catalysts. These catalysts may be used as the complexes having ligands such as phosphine and carbonyl, and also as the metal elements themselves. In using the catalyst as a complex, the complex may be formed in advance before using as a catalyst or may be formed in a reaction system by adding separately to the reaction system.

Preferred catalysts include palladium complexes such as tetrakis(triphenylphosphine)palladium, palladium metal such as palladium/carbon, cobalt/carbonyl complexes such as dicobalt octacarbonyl and the like. Catalysts of the invention may be used in a supported form on a support. Supports to be used include activated carbon, alumina and the like.

In the method of the invention, use of solvent is preferable. Preferred solvents to be used should be non-reactive and should have sufficient dissolving power for raw materials and reaction products.

The solvents to be used in the method of the invention include polar solvents such as acetone and dimethylfolmamide (DMF) and ether type solvents such as tetrahydrofurane THF) and dioxane.

Pressure under which reaction of the invention is carried out may be either atmospheric or pressurized, however, the latter is preferable. Preferred reaction pressure is from 0.1 to 6.0 MPa, more preferably from 0.5 to 5.0 MPa. If carbonyl complexes are used as the catalyst, an addition of carbon monoxide is preferable, and partial pressure of the carbon monoxide is from 0.5 to 10.0 MPa, preferably from about 1.0 to about 6.0 MPa.

Reaction temperature in the invention may be selected within a range from room temperature to boiling point of the solvent. Preferred reaction temperature is from 25 to 100° C., more preferably from 25 to 80° C.

Target, aldehydes can be isolated and purified from the reaction mixtures obtained using known methods. Methods for isolation and purification include usual processes such as distillation and chromatography.

Method of the invention has wider application range and is possible to make selection range for raw compounds still wider, because it enables not only to prepare target aldehydes in high yields and selectivities but also to be used both in homogeneous and heterogeneous reaction systems under mild reaction conditions, and thus it is industrially advantageous.

EXAMPLES

The invention is further illustrated by reference to the following examples which are not intended in any way to limit the scope of the invention.

Example 1~9

A 100 cm$^3$ stainless autoclave was purged with argon gas and charged with a catalyst (0.02 mmol), solvent (5 cm$^3$), carboxylic acid (2 mmol) and dehydrating agents shown in Table 1, then pressurized at 3.0 MPa with hydrogen at room temperature. And the reaction system was stirred for 24 hr at 80° C. The reactor was then cooled to the temperature below room temperature, hydrogen pressure was released and the reaction solution was analyzed by $^1$H-NMR and gas chromatography mass spectrometry.

The reaction conditions are shown below by the following reaction formula.

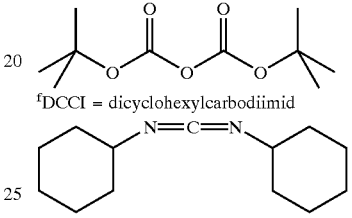

Results are shown in Table 1.

TABLE 1

Catalytic hydrogenation reactions of caprylic acid
Study on dehydrating agent, temperature and hydrogen pressure[a]

| Example No. | ($^t$BuCO)$_2$O Equivalent | H$_2$ Pressure Mpa | Temperature ° C. | Yield[b] (%) 3[c] | 4[c] |
|---|---|---|---|---|---|
| 1 | 3 | 3.0 | 80 | 98 | 23 |
| 2 | 2 | 3.0 | 80 | 92 | 13 |
| 3 | 1.5 | 3.0 | 80 | 90 | 7 |
| 4 | 1 | 3.0 | 80 | 78 | 4 |

TABLE 1-continued

Catalytic hydrogenation reactions of caprylic acid
Study on dehydrating agent, temperature and hydrogen pressure[a]

| Example No. | ($^t$BuCO)$_2$O Equivalent | H$_2$ Pressure Mpa | Temperature ° C. | Yield[b] (%) 3[c] | 4[c] |
|---|---|---|---|---|---|
| 5 | 3 | 0.5 | 80 | 47 | 18 |
| 6 | 3 | 3.0 | 50 | 68 | 7 |
| 7 | Boc$_2$O[e]3 | 3.0 | 80 | 54 | — |
| 8[d] | Boc$_2$O3 | 3.0 | 80 | 68 | — |
| 9 | DCCI[f]3 | 3.0 | 80 | 31 | — |

[a]Reaction conditions: Refer to body of the example.
[b]Yield based on caprylic acid
[c]Calculated based on $^1$H NMR.
[d]Reaction time: 48 hours.
[e]Boc2O = di-(tert-butyl) pyrocarbonate

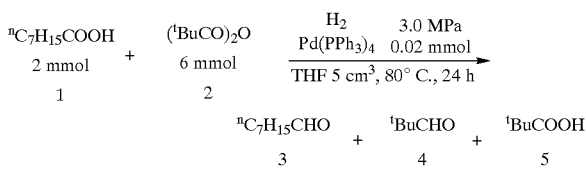

[f]DCCI = dicyclohexylcarbodiimid

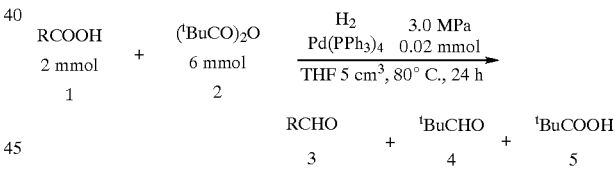

Results in Table 1 demonstrate that various types of dehydrating agents can be used but trimethylacetic acid provides the highest yield, and aldehydes can be obtained almost quantitatively when 3 equivalents of trimethylacetic acid to each carboxylic acid is added.

Examples 10~20

Using carboxylic acids shown in Table 2, corresponding aldehydes were prepared by the method as described in example 1. The reactions are shown by the following general formula. Results are shown in Table 2.

$$\text{RCOOH} + (^t\text{BuCO})_2\text{O} \xrightarrow[\text{THF 5 cm}^3, 80° \text{C., 24 h}]{\text{H}_2 \quad 3.0 \text{ MPa} \quad \text{Pd(PPh}_3)_4 \quad 0.02 \text{ mmol}} \text{RCHO} + {}^t\text{BuCHO} + {}^t\text{BuCOOH}$$

2 mmol   6 mmol                                                        3            4            5
  1         2

Results in Table 2 demonstrate the following. Aliphatic carboxylic acids of the substrates with primary α position generated aldehydes almost quantitatively. In this case, cis inner olefins of oleic acid and erucic acid were not hydrogenated, as confirmed by $^1$H-NMR. In the case of trans cinnamic acid, the yield was improved by using Pd(OAc)$_2$/ 2PPh$_3$ with Pd/P ratio of 1/2 as a catalyst. In 10-undecenoic acid with terminal olefin, carboxyl group was converted to formyl group in high yield. However, isomerization of the terminal olefin to inner olefin was observed, and generation of hydrogenated compound at the olefin moiety was also suggested by $^1$H-NMR. Substrates with many substituents at α position showed lower yields. In the cases of 2-phenylpropionic acid and diphenyl acetic acid, a decarbonylation from acyl palladium complexes, which were regarded as reaction intermediates, occurred and generated mainly styrene and diphenylmethane respectively as by-products, thus the yields for aldehydes were significantly low. Trimethylacetic acid added as a dehydrating agent, was hardly hydrogenated under these reaction conditions.

TABLE 2

Examples of catalytic hydrogenation reactions of aliphatic carboxylic acids[a]

| Example No. | Carboxylic Acid | Residual Products[b] (%) | | Yield[b] (%) | | | By-Product |
|---|---|---|---|---|---|---|---|
| | | 1[d] | 2[d] | 3[c] | 4[c] | 5[d] | |
| 10 | [A]C₇H₁₅COOH | 0 | 148 | 98 | 23 | 260 | |
| 11 | Ph∼∼COOH | 0 | 154 | 99 | 25 | 282 | |
| 12 | oleic acid | 0 | 142 | 99[e] | 26 | 290 | |
| 13 | erucic acid | 0 | 154 | 96[e] | 21 | 276 | |
| 14[g] | Ph∼═COOH | | 190 | 84 | >1 | 184 | |
| 15 | ═∼∼∼∼∼COOH | | 175 | (87) | 13 | 219 | olefin[e] external 48% internal 38% hydrogenated (14%) |
| 16 | (branched)COOH | 0 | 147 | 64 | 39 | 227 | |
| 17[h] | (cyclohexyl)COOH | | | 82 | 35 | | |
| 18[i] | Ph(iPr)COOH | | | | 4 | 17 | Ph—═ 53%[c] |
| 19 | Ph₂CHCOOH | 0 | 156 | 13 | 21 | 269 | Ph₂CH₂[f] 17%[d] |
| 20 | Acid Blank | — | 235 | — | 40 | 89 | |

[a]Practical reaction conditions: Refer to body of the example.
[b]Yield based on carboxylic acid
[c]Calculated based on ¹H NMR.
[d]Calculated based on gas chromatography analysis
[e]According to ¹H NMR, no change was observed in the internal double bonds
[f]Confirmed by gas chromatography - mass spectrometry (GCMS).
[g]Catalyst: Pd(OAc)₂/2PPh₃ instead of Pd(PPh₃)₄ was used.
[h]Reaction time: 48 hours
[i]Hydrogen pressure: 6.0 Mpa oleic acid = ais-9-octadecenoic acid 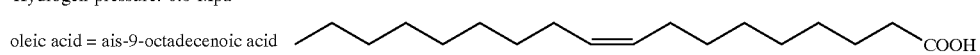

erucic acid = ais-13-dococenoic acid 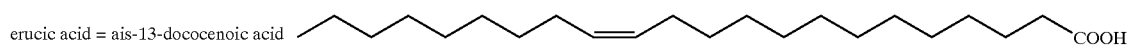

Examples 21~27

Using various aromatic carboxylic acids shown in Table 3, corresponding aldehydes were prepared by the method as described in example 1. The reactions are shown by the following general formula. Results are shown in Table 3.

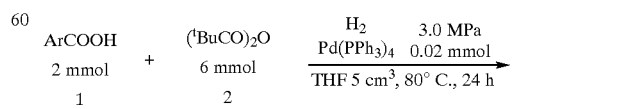
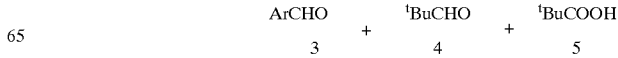

TABLE 3

Examples of catalytic hydrogenation reactions of aromatic carboxylic acids[a]

| Example No. | Carboxylic Acid | Residual Products[b] (%) | | Yield[b] (%) | | | By-Product |
|---|---|---|---|---|---|---|---|
| | | 1[d] | 2[d] | 3[c] | 4[c] | 5[d] | |
| 21 | PhCOOH | tr | 142 | 91 | 31 | 260 | (PhCO)$_2$O[f] 5%[d] |
| 22 | NC—C$_6$H$_4$—COOH | 0 | 143 | 99 | 26 | 269 | |
| 23 | Bu$^t$—C$_6$H$_4$—COOH | 0 | 161 | 99 | 27 | 265 | |
| 24[e] | MeO—C$_6$H$_4$—COOH | 0 | 126 | 95 | 38 | 269 | |
| 25 | 3-PhO-C$_6$H$_4$-COOH | 0 | 143 | 97 | 21 | 251 | Ph$_2$O[f] |
| 26 | 2-Me-C$_6$H$_4$-COOH | | 187 | 30 | 20 | 202 | |
| 27[g] | 2-naphthoic acid | | 198 | 60 | 13 | 158 | naphthalene[f] 10%[d] |

[a]Practical reaction conditions: Refer to body of the example.
[b]Yield based on carboxylic acid.
[c]Calculated based on $^1$H NMR.
[d]Calculated based on gas chromatographic analysis
[e]Reaction time: 48 hours
[f]Confirmed by gas chromatography - mass spectrometry (GCMS)
[g]Hydrogen pressure: 6.0 Mpa Results in Table 3 demonstrate that aromatic carboxylic acids with substituents at m- or p-positions were hydrogenated successfully. In naphthoic acid, it was found that decarbonylation reaction occurred also as a side reaction.

Examples 28~32

Using various polybasic acids shown in Table 4, corresponding aldehydes were prepared by the method as described in example 1. The reactions are shown by the following general formula. Results are shown in Table 4.

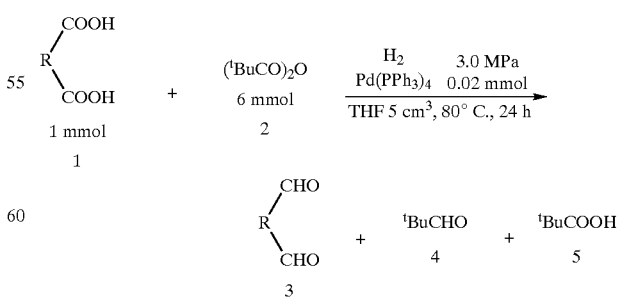

Results in Table 4 demonstrate that carboxyl groups were also converted efficiently to formyl groups similarly to polybasic acids.

TABLE 4

Examples of catalytic hydrogenation reactions of polybasic acids[a]

| Example No. | Carboxylic Acid | Residual Products[b] (%) 1[d] | 2[d] | Yield[b] (%) 3[c] | 4[c] | 5[d] | By-Product |
|---|---|---|---|---|---|---|---|
| -28 | HOOC(CH$_2$)$_n$COOH, n = 10 | 0 | 146 | 99 | 24 | -272 | |
| 29 | HOOC—C$_6$H$_4$—COOH (para) | 0 | 161 | 99 | 18 | 233 | |
| 30 | HOOC—C$_6$H$_4$—COOH (meta) | 0 | 169 | 94 | 13 | 230 | |
| 31 | C$_6$H$_4$(COOH)$_2$ (ortho) | 0 | 202 | 0 | 36 | 152 | phthalic anhydride[e] quantitative |
| 32 | 1,3,5-benzenetricarboxylic acid | | 153 | 86[g] | 17 | 228 | 3-OHC-C$_6$H$_4$-CHO[e] 6%[d] |

[a]Practical reaction conditions: Refer to body of the example except following. 1 mmol each of carboxylic acids for examples 28–31, and 0.67 mmol of carboxylic acid for example 32.
[b]Yield based on carboxylic acid
[c]Calculated based on $^1$H NMR
[d]Calculated based on gas chromatographic analysis.
[e]Confirmed by gas chromatography - mass spectrometry (GCMS).

Example 33

Corresponding aldehydes were prepared as described in example 1 by the method shown by the following reaction formula. Yield was 99%.

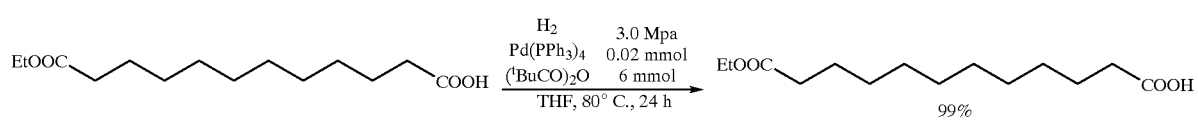

Example 34

Corresponding aldehydes were prepared as described in example 1 by the method shown by the following reaction formula. Yield was 99%.

Example 35

Corresponding aldehydes were prepared as described in example 1 by the method shown by the following reaction formula. Yield was 84%.

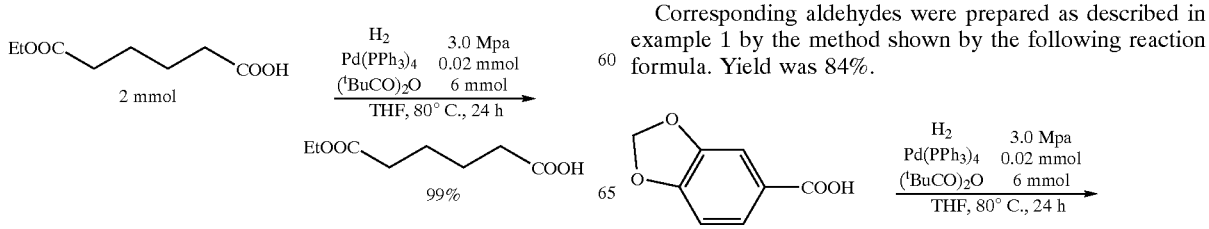

-continued

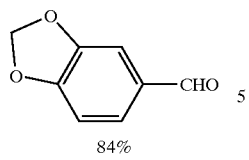

84%

Example 36

Corresponding aldehydes were prepared from β-pyridinecarboxylic acid as described in example 1 by the method shown by the following reaction formula. Yield was 99%.

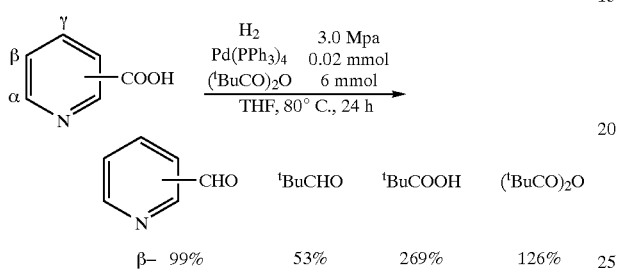

| | β– 99% | 53% | 269% | 126% |

Examples 37~38

Corresponding aldehydes were prepared from furancarboxylic acids as described in example 1 by the method shown by the following reaction formula. Yields in 3-furancarboxylic acid and 2-furancarboxylic acid were 90% and 87%, respectively.

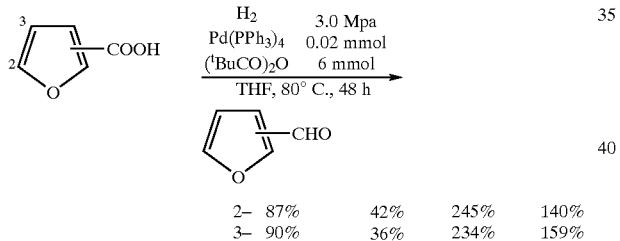

| 2– | 87% | 42% | 245% | 140% |
| 3– | 90% | 36% | 234% | 159% |

Examples 39~40

Corresponding aldehydes were prepared from thiophenecarboxylic acids as described in example 1 by the method shown by the following reaction formula. Yields in 2-thiophenecarboxylic acid and 3-thiophenecarboxylic acid were 72% and 73%, respectively.

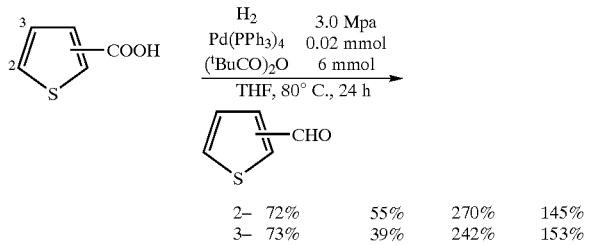

| 2– | 72% | 55% | 270% | 145% |
| 3– | 73% | 39% | 242% | 153% |

Example 41

Using cobalt octacarbonyl [$Co_2(CO)_8$] as a catalyst and under hydrogen pressure of 5.0 MPa and CO pressure of 5.0 MPa, caprylaldehyde was obtained as described in example 1 by the method shown by the following reaction formula in yield of 20%.

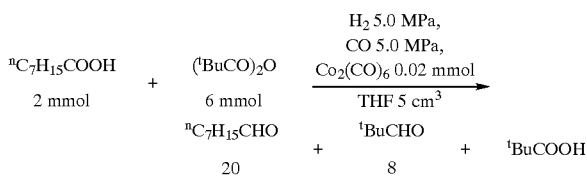

Examples 42~45

Corresponding benzaldehyde halides were prepared by hydrogenation of benzoic acid halides shown by the following formula, as described in example 1. Yields were 78%, 99%, 93% and 99%, respectively.

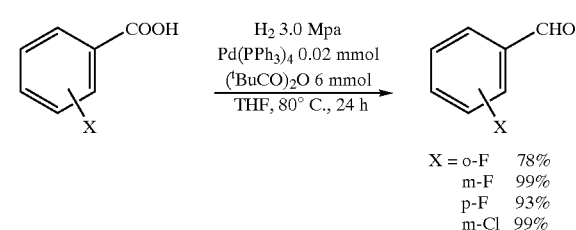

X = o-F   78%
    m-F   99%
    p-F   93%
    m-Cl  99%

Examples 46~47

Corresponding aldehydes were prepared by hydrogenation of ketocarboxylic acids shown by the following formula, as described in example 1. Yields were 97% and 85%, respectively.

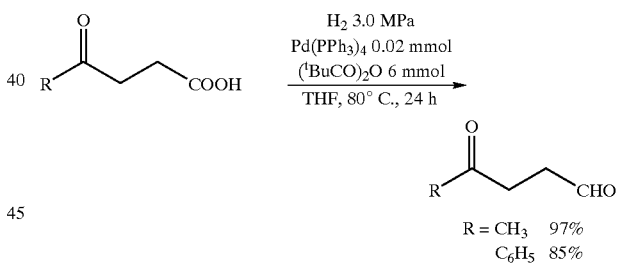

R = $CH_3$   97%
    $C_6H_5$  85%

Example 48

Corresponding aldehyde was prepared by hydrogenation of α-naphthalenecarboxylic acid shown by the following formula, as described in example 1. Yield was 50%.

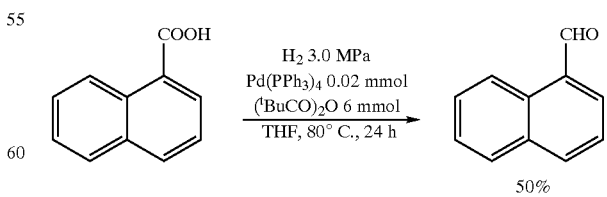

50%

Example 49

In this catalytic reaction, a mixture of palladium acetate and 5 equivalents of tri(4-methylphenyl)phosphine to the palladium compound were used as a catalyst, and the reaction was carried out in acetone solvent by the following formula as described in example 1. The reaction was found to proceed fast.

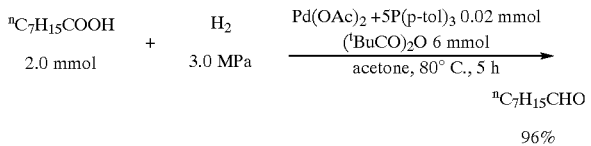

Example 50

Using a solid catalyst of 10% palladium supported on activated carbon as a catalyst, the reaction was carried out as described in example 1 by the following formula, and the target octanal was prepared with yield of 15%

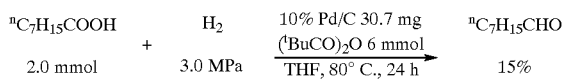

INDUSTRIAL APPLICABILITY

According to the method of the invention, various organic carboxylic acids such as aromatic, heterocyclic or aliphatic carboxylic acids can be hydrogenated to corresponding aldehydes simply and in high yields. This method provides advantageous synthesis methods for various organic compounds because aldehydes can be converted easily to other derivatives by aldol reaction and the like.

What is claimed is:

1. A method for preparation of organic aldehydes by reducing corresponding carboxylic acids with molecular hydrogen in the presence of a catalyst, wherein the said reaction is performed in the presence of an anhydride dehydrating agent.

2. A method according to claim 1, wherein the said dehydrating agent is carboxylic anhydride.

3. A method according to claim 2, wherein the said carboxylic anhydride is aliphatic carboxylic anhydride.

4. The method according to claim 1, wherein the said reaction is performed in the presence of solvent.

5. The method according to claim 1, wherein the said catalyst is palladium catalyst.

6. The method according to claim 5, wherein the said palladium catalyst is a zero valent palladium complex.

7. The method according to claim 1, wherein the said catalyst is a solid catalyst.

8. The method according to claim 4, wherein the said reaction is performed at the temperature from 25 to 100° C.

9. The method according to claim 8, wherein the said reaction is performed under the pressure from 0.1 to 6.0 MPa.

10. The method according to claim 1, wherein the said dehydrating agent is carboxylic anhydride and the said catalyst is palladium catalyst.

11. The method according to claim 10, wherein the said carboxylic anhydride is aliphatic carboxylic anhydride.

12. The method according to claim 10, wherein the said carboxylic anhydride is aliphatic carboxylic anhydride and the said palladium catalyst is a zero valent palladium complex.

13. The method according to claim 1, wherein the said dehydrating agent is carboxylic anhydride, the said catalyst is palladium catalyst and the said reaction is performed in the presence of solvent.

14. The method according to claim 13, wherein the said reaction is performed at the temperature from 25 to 100° C.

15. The method according to claim 13 or 14, wherein the said reaction is performed under the pressure from 0.1 to 6.0 MPa.

16. The method according to claim 13, wherein the said carboxylic anhydride is aliphatic carboxylic anhydride and the said palladium catalyst is a zero valent palladium complex.

17. The method according to claim 13, wherein the said carboxylic anhydride is aliphatic carboxylic anhydride, the said palladium catalyst is a zero valent palladium complex and the said reaction is performed at the temperature from 25 to 100° C.

18. The method according to claim 17, wherein the said reaction is performed under the pressure from 0.1 to 6.0 MPa.

* * * * *